United States Patent [19]

Rose et al.

[11] Patent Number: 4,756,715
[45] Date of Patent: Jul. 12, 1988

[54] HAIR-DYEING PREPARATIONS CONTAINING SUBSTANTIVE NITRODIPHENYLAMINE DERIVATIVES

[75] Inventors: David Rose, Hilden; Edgar Lieske, Duesseldorf; Norbert Maak, Neuss, all of Fed. Rep. of Germany

[73] Assignee: Henkel Kommanditgesellschaft auf Aktien, Duesseldorf, Fed. Rep. of Germany

[21] Appl. No.: 922,610

[22] Filed: Oct. 24, 1986

[30] Foreign Application Priority Data

Oct. 24, 1985 [DE] Fed. Rep. of Germany ....... 3537765

[51] Int. Cl.$^4$ .................. A61K 7/13; C07C 87/54
[52] U.S. Cl. ................................ 8/429; 8/405;
8/407; 8/409; 8/414; 260/505 C; 260/508;
562/435; 564/433; 564/434
[58] Field of Search ............. 260/505 C, 508;
562/435; 564/433, 434; 8/405, 407, 408, 409,
414, 429

[56] References Cited

U.S. PATENT DOCUMENTS 2,687,431 8/1954 Marschall ........................ 260/509
3,930,792 1/1976 Alperin et al. ...................... 8/415
3,950,127 4/1976 Halasz et al. ........................ 8/414

FOREIGN PATENT DOCUMENTS 1569808 7/1970 Fed. Rep. of Germany .
2830497 1/1980 Fed. Rep. of Germany .
2216271 2/1973 France .
2360559 8/1977 France .
1588215 4/1981 United Kingdom .

OTHER PUBLICATIONS

Jackson et al., *American Chem. Journal*, vol. 19, Jan. 1987, (pp. 1+).
Ullman, *Ann.* vol. 366, 1909, (pp. 79–118).
Chemical Abstracts, 72:110950d, p. 350.
Chemical Abstracts, 92:203416n, p. 321.
Chemical Abstracts, 88:89301m, p. 487.
Chemical Abstracts, 79:104940d, p. 400.
Beilsteins Handbuch Der Organischen Chemie, F. Richter, Berlin, Germany, 1933, p. 564.
European Patent Office Search Report, (RE: Ser. No. 922,609).
European Patent Office Search Report, (RE: Ser. No. 922,610).

*Primary Examiner*—Paul Lieberman
*Assistant Examiner*—Linda D. Skaling
*Attorney, Agent, or Firm*—Ernest G. Szoke; Henry E. Millson, Jr.; Mark A. Greenfield

[57] ABSTRACT

Novel substituted nitrodiphenylamines and substantive hair dye preparations containing them or containing nitrodiphenylamines with different substituents. The dyes result in yellow to copper-colored shades of high intensity and fastness and are more soluble in water than known nitroanilines dyes.

36 Claims, No Drawings

HAIR-DYEING PREPARATIONS CONTAINING SUBSTANTIVE NITRODIPHENYLAMINE DERIVATIVES

BACKGROUND OF THE INVENTION

1. Field of the Invention

This invention relates to hair-dyeing preparations containing substantive hair dyes.

2. Statement of Related Art

Hair-dyeing preparations of the type in question contain substantive hair dyes in a cosmetic carrier. In many cases, such hair-dyeing preparations additionally contain oxidation dye precursors to produce certain shades. The cosmetic carriers used for the substantive hair dyes and oxidation dye precursors, if any, are creams, emulsions, gels, shampoos, foam aerosols or other preparations suitable for application to the hair.

In addition to the oxidation dyes, which are formed by the oxidative coupling of one or more developer components with one another or with one or more coupler components, substantive hair dyes play a prominent part in the dyeing of hair. Substantive dyes have the advantage of being used without the addition of oxidizing agents. The substantive dyes used are predominantly nitrobenzene derivative compounds. They are used either on their own or in combination with other substantive dyes, such as anthraquinone dyes, indophenols, triphenylmethane dyes, cationic azo dyes, or with oxidation dyes.

Good hair-dyeing preparations have to form the required shades with sufficient intensity. They must be readily absorbed by human hair without excessively staining the scalp. The dye finishes produced by them must show high stability to light, heat, perspiration, shampoos and the chemicals used in the permanent waving of hair. Finally, they should be safe to use from the toxicological and dermatological viewpoint.

Among the substantive nitrobenzene derivatives, the nitroanilines and derivatives thereof play an important part because some of these dyes produce intensive, light-stable dye finishes. However, the known substantive nitroaniline dyes have disadvantages in that, on the one hand, they show only limited solubility in water, which leads to problems during formulation of the hair-dyeing preparations, and on the other hand they are not sufficiently fast to washing, i.e. the dye finishes fade considerably after repeated washing. In addition, substantive dyes are required to show high compatibility with other dyes, for example with oxidation dye precursors and with the components normally used in oxidation hair-dyeing preparations because substantive dyes and oxidation dyes are often combined with one another for color modification. Accordingly, high stability to reducing agents and oxidizing agents is necessary.

DESCRIPTION OF THE INVENTION

Other than in the operating examples, or where otherwise indicated, all numbers expressing quantities of ingredients or reaction conditions used herein are to be understood as modified in all instances by the term "about".

It has been found that hair-dyeing preparations satisfying the above requirements satisfactorily contain as substantive hair dyes compounds corresponding to the general formula

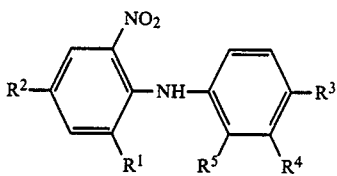

wherein:

(A) one of $R^1$ or $R^2$ is nitro and the other is —$SO_3H$ or —COOH; and (B)
(1) $R^3$, $R^4$ and $R^5$ are, independently of one another, hydrogen or a $C_{1-4}$ alkyl; or (2) two of $R^3$, $R^4$, and $R^5$ are, independently of one another, hydrogen or a $C_{1-4}$ alkyl, and the remaining is hydroxyl or $NR^6R^7$ where $R^6$ and $R^7$ are, independently of one another, hydrogen, a $C_{1-4}$ alkyl, or a $C_{2-4}$ hydroxyalkyl; or (3) one of $R^3$, $R^4$, or $R^5$ is hydrogen or a $C_{1-4}$ alkyl, another is hydroxyl or $NR^6R^7$ where $R^6$ and $R^7$ are, independently of one another, hydrogen, a $C_{1-4}$ alkyl, or a $C_{2-4}$ hydroxyalkyl, and the remaining is hydroxymethyl, a $C_{1-4}$ alkoxy, or chlorine;

or their water-soluble salts.

When the disclosed nitrodiphenylamine derivatives are used as hair dyes, it is preferred that the $R^3$ moiety of formula I is hydroxyl or —$NR^6R^7$, as defined above.

Particularly preferred substituents are:

at $R^3$: hydroxy, amino, methylamino, dimethylamino, diethylamino, N-ethyl-N-β-hydroxyethylamino, or N,N-bis-(β-hydroxyethyl)-amino;

at $R^4$: hydrogen, methyl, dimethyl, or hydroxymethyl;

at $R^5$: hydrogen, methyl, methoxy, or chlorine.

The dyes corresponding to general formula I produce yellow to copper shades of high intensity, high fastness to light, and good resistance to leaching upon washing the hair. In addition, they show better solubility in aqueous-alkaline medium than known nitroaniline dyes. The compounds corresponding to general formula I are dermatologically and toxicologically safe and are therefore particularly suitable for use in hair-dyeing preparations.

Compounds corresponding to general formula I, in which $R^3$, $R^4$ and $R^5$ are hydrogen, are known from the literature. The other compounds corresponding to general formula I are generally produced by reaction of a 1-chloro-2-nitrobenzene derivative corresponding to the following formula

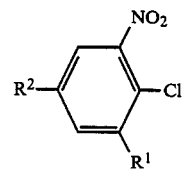

with an aniline derivative corresponding to the following formula

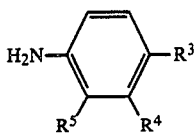
(III)

with elimination of HCl in the presence of a base.

In formulae II and III above, $R^1$ to $R^5$ have the meanings defined for formula I.

Compounds corresponding to general formula I, in which $R^3$ is hydroxyl or an amino ($NR^6R^7$, where $R^6$ and $R^7$ are as defined above) are particularly suitable and are not known from the literature.

Accordingly, the present invention also relates to compounds per se corresponding to general formula I, wherein:

(C) one of $R^1$ or $R^2$ is nitro and the other is $-SO_3H$ or $-COOH$;

(D) $R^3$ is hydroxyl or $NR^6R^7$ where $R^6$ and $R^7$ are, independently of one another, hydrogen, a $C_{1-4}$ alkyl, or a $C_{2-4}$ hydroxyalkyl; and (E)
 (1) $R^4$ and $R^5$ are, independently of one another, hydrogen or a $C_{1-4}$ alkyl, or
 (2) one of $R^4$ or $R^5$ is hydrogen or a $C_{1-4}$ alkyl, and the other is hydroxymethyl, a $C_{1-4}$ alkoxy, or chlorine;

or their water-soluble salts.

In the context of the invention, water soluble salts are primarily understood to be the salts of strong bases, such as alkali salts, for example sodium or potassium, or ammonium, $C_{2-4}$-alkanolammonium such as monoethanolammonium, triethanolammonium or isopropanolammonium.

The hair-dyeing preparations according to the invention may contain at least one of the substantive nitrodiphenylamine derivatives corresponding to general formula I either alone or in combination with known substantive dyes, for example with other nitrobenzene derivatives, anthraquinone dyes, triphenylmethane or azo dyes. In addition, the substantive dyes of general formula I, by virtue of their high resistance to reducing agents and oxidizing agents, are also eminently suitable for combination with oxidation dye precursors, i.e. for modifying the shades of oxidation hair-dyeing preparations. Oxidation hair-dyeing preparations contain as dye precursors developer components which form the oxidation dyes by oxidative coupling with one another or with suitable coupler components. The developer components used are primary aromatic amines containing another free or substituted hydroxy or amino moiety in the para or ortho position, diaminopyridine derivatives, heterocyclic hydrazones, 4-aminopyrazolone derivatives and 2,4,5,6-tetra-aminopyrimidine and derivatives thereof. The coupler components used are m-phenylenediamine derivatives, napthols, resorcinol and resorcinol derivatives, pyrazolones and m-aminophenols.

To produce the hair-dyeing preparations according to the invention the substantive hair dyes and the oxidation dye precursors, if any, are incorporated in suitable cosmetic carriers, for example in creams, emulsions, gels, surfactant-containing foaming solutions such as shampoos, aerosol foams, or other preparations which are suitable for application to the hair, preferably with an aqueous base.

Standard constituents of cosmetic preparations such as these include wetting agents and emulsifiers, such as anionic, nonionic or ampholytic surfactants, for example fatty alcohol sulfates, alkane sulfonates, olefin sulfonates, fatty alcohol polyglycolether sulfates, ethylene oxide adducts with fatty alcohols, fatty acids and alkylphenols, sorbitan fatty acid esters and fatty acid partial glycerides, fatty acid alkanolamides; and also thickeners such as methyl or hydroxyethyl cellulose, starch, fatty alcohols, paraffin oils, fatty acids, perfume oils and hair-care additives such as water-soluble cationic polymers, protein derivatives, pantothenic acid and cholesterol. The constituents of the cosmetic carriers are used in the usual quantities for preparing the hair-dyeing preparations according to the invention. For example, emulsifiers are used in concentrations of from 0.5 to 30% by weight and thickeners in concentrations of from 0.1 to 25% by weight, based on the preparation as a whole.

In the hair-dyeing preparations according to the invention, the substantive hair dyes corresponding to general formula I are used in quantity of from 0.01 to 5.0% by weight and preferably in a quantity of from 0.1 to 2% by weight, based on the hair-dyeing preparation as a whole. Substantive hair dyes other than those of formula I may optionally be present in a total quantity of 0 to 5%, preferably 0.01 to 5%, all by weight based upon the preparation as a whole. In addition, known oxidation hair dye precursors (developers and couplers) optionally may be present in a total quantity of from 0 to 5%, preferably 0.01 to 5%, more preferably 1 to 3% by weight, based on the total weight of the hair preparation.

If the hair-dyeing preparation according to the invention contains oxidation dye precursors, it is advisable also to add a small quantity of a reducing agent, for example from 0.5 to 2.0% by weight of sodium sulfite, to stabilize the oxidation dye precursors. In this case, an ozidizing agent is added to the hair-dyeing preparation before use in order to initiate oxidative development of the oxidation dye precursors. Suitable oxidizing agents are, in particular, hydrogen peroxide or adducts thereof with urea, melamine or sodium borate and also mixtures of these hydrogen peroxide adducts with potassium peroxydisulfate.

The hair-dyeing preparations according to the invention may be used in a mildly acidic, neutral or alkaline medium, irrespective of the cosmetic carrier used, such as a cream, gel or shampoo. The hair-dyeing preparations are preferably in the pH-range from 8 to 10. They may be used at temperatures of from 15° C. to 40° C. After a contact time of around 30 minutes, the hair-dyeing preparation is removed by rinsing from the hair to be dyed. The hair is then washed with a mild shampoo and dried. Washing with a shampoo is unnecessary when a carrier of high surfactant content, for example a dye shampoo, is used.

Hair dye finishes of high intensity, good fastness properties, particularly to washing, and high stability to bleeding and changes in color during shampooing may be obtained with the hair-dyeing preparations according to the invention. The following Examples are intended to illustrate the invention without limiting it in any way.

EXAMPLES
Production Examples

1. 2,6-dinitro-4'-dimethylaminodiphenylamine-4-sulfonic acid, K-salt

A mixture of 5 g 4-chloro-3,5-dinitrobenzene sulfonic acid, K-salt (0.016 mol), 2,2 g N,N-dimethyl-p-phenylenediamine (0.016 mol) and 1.1 g potassium carbonate (0.008 mol) in 50 ml water was refluxed for 1 hour. After cooling, the deposit was filtered off. An ochre-brown powder was obtained.

UV-spectrum (pH-9.5)$\lambda_{MAX}$=437 nm

2. 2,6-dinitro-4'-aminodiphenylamine-4-sulfonic acid, K-salt

Preparation was carried out in the same way as in Example 1, except that 1.73 g p-phenylenediamine (0.016 mol) was used instead of N,N-dimethyl-p-phenylenediamine.

UV-spectrum (pH=9.5)$\lambda_{MAX}$=431 nm

3. 2,6-dinitro-4'-methylaminodiphenylamine-4-sulfonic acid, K-salt

Preparation was carried out in the same way as in Example 1, except that 3.1 g N-methy-p-phenylenediamine (0.016 mol) was used instead of N,N-dimethyl-p-phenylenediamine.

UV-spectrum (pH=9.5)$\lambda_{MAX}$=441 nm

4. 2,6-dinitro-2°-methyl-4'-aminodiphenylamine-4-sulfonic acid, K-salt

Preparation was carried out in the same way as in Example 1, except that 3.5 g p-tolylenediamine sulfate (0.016 mol) was used instead of N,N-dimethyl-p-phenylenediamine. Red-brown powder.

UV-spectrum (pH=9.5)$\lambda_{MAX}$=449 nm

5. 2,6-dinitro-4'-N,N-bis-(β-hydroxyethyl)-aminodiphenylamine-4-sulfonic acid, K-salt Preparation was carried out in the same way as in Example 1, except that 5.2 g N,N-bis-(β-hydroxyethyl)-p-phenylenediamine (0.016 mol) was used instead of N,N-dimethyl-p-phenylenediamine. Red-brown powder.

UV-spectrum (pH=9.5)$\lambda_{MAX}$=443 nm

6. 2,6-dinitro-2'-chloro-4'-aminodiphenylamine-4-sulfonic acid, K-salt

Preparation was carried out in the same way as in Example 1, except that 3,85 g 2-chloro-p-phenylenediamine sulfate (0.016 mol) was used instead of N,N-dimethyl-p-phenylenediamine. Red-brown crystals.

IR-spectrum (KBr; cm$^{-1}$): 1620, 1565, 1530, 1505, 1420, 1340, 1270, 1240, 1205, 1150, 1130, 1110, 1045, 920, 910, 895, 825

7. 2,6-dinitro-2',3'-dimethyl-4'-aminodiphenylamine-4-sulfonic acid, K-salt Preparation was carried out in the same way as in Example 1, except that 2.2 g (0.016 mol) 2,3-dimethyl-p-phenylenediamine was used instead of N,N-dimethyl-p-phenylenediamine. Brown crystals.

IR-spectrum (KBr; cm$^{-1}$): 1620, 1565, 1530, 1490, 1420, 1345, 1270, 1210, 1180, 1105, 1050, 920, 905, 835, 820

8. 2,6-dinitro-3'-hydroxymethyl-4'-aminodiphenylamine-4-sulfonic acid, K-salt Preparation was carried out in the same way as in Example 1, except that 3,8 g 2,5-diaminobenzylalcohol (0.016 mol) was used instead of N,N-dimethyl-p-phenylenediamine. Brown crystals.

UV-spectrum (pH=9.5)$\lambda_{MAX}$=427 nm

9. 2,6-dinitro-2'-methoxy-4'-aminodiphenylamine-4-sulfonic acid, K-salt

Preparation was carried out in the same way as in Example 1, except that 3,8 g 2,5-diaminoanisole sulfate (0.016 mol) was used instead of N,N-dimethyl-p-phenylenediamine. Brown crystals.

UV-spectrum (pH=9.5)$\lambda_{MAX}$=424 nm

10. 2,6-dinitro-4'-hydroxydiphenylamine-4-sulfonic acid, K-salt

Preparation was carried out in the same way as in Example 1, except that 1.75 g p-aminophenol (0.016 mol) was used instead of N,N-dimethyl-p-phenylenediamine.

11. 2,6-dinitro-4'-ethyl-N-β-hydroxyethylaminodiphenylamine-4-sulfonic acid, K-salt Preparation was carried out in the same way as in Example 1, except that 4.5 g N-ethyl-N-β-hydroxyethyl-p-phenylenediamine sulfate was used instead of N,N-dimethyl-p-phenylenediamine. Black crystals.

UV-spectrum (pH=9.5)$\lambda_{MAX}$=446 nm

12. 2,6-dinitro-2'-methyl-4'-N,N-diethylaminodiphenylamine-4-sulfonic acid, K-salt Preparation was carried out in the same way as in Example 1, except that 3.4 g N,N-diethyl-2-methyl-p-phenylenediamine dihydrochloride (0.016 mol) was used instead of N,N-dimethyl-p-phenylenediamine. Black crystals.

IR-spectrum (KBr; cm$^{-1}$): 1620, 1565, 1510, 1470, 1450, 1430, 1400, 1380, 1355, 1340, 1265, 1240, 1200, 1115, 1100, 1080, 1045, 930, 905, 870, 840.

13. 2,4-dinitro-4'-dimethylaminodiphenylamine-4-carboxylic acid

A mixture of 5 g N,N-dimethyl-p-phenylenediamine (0.024 mol), 6 g 3,5-dinitro-2-chlorobenzoic acid (0.024 mol) and 3.3 g potassium carbonate in 40 ml water was stirred for 2 hours at room temperature. The deposit was filtered off. Curry-colored crystals.

Melting point 249° C. (with decomposition)

14. 2,6-dinitro-4'-aminodiphenylamine-4-carboxylic acid

A mixture of 5 g 4-chloro-3,5-dinitrobenzoic acid (0.024 mol), 3 g p-phenylenediamine (0.024 mol) and 5.4 g sodium acetate was refluxed in 60 ml water. After cooling, the deposit was filtered off and thoroughly boiled several times with water. Residue: brown crystals.

Melting point 160° C. (with decomposition)

15.
2,6-dinitro-4'-amino-3'-methyldiphenylamine-4-carboxylic acid

Preparation was carried out in the same way as in Example 14 except that 4.4 g p-tolylenediamine sulfate (0.02 mol) was used instead of p-phenylenediamine. Light brown crystals.

Melting point 188° C. (with decomposition)

16.
2,6-dinitro-4'-N,N-dimethylaminodiphenylamine-4-carboxylic acid

Preparation was carried out in the same way as in Example 14 except that 5 g (0.02 mol) N,N-dimethyl-p-phenylenediamine dihydrochloride was used instead of p-phenylenediamine. Black crystals.

Melting point 228° to 232° C.

17. 2,6-dinitro-4'-hydroxydiphenylamine-4-carboxylic acid

Preparation was carried out in the same way as in Example 14, except that 2.18 g p-aminophenol (0.02 mol) was used instead of p-phenylenediamine. Orange-brown crystals.

Melting point 240° C.

18. 2,4-dinitro-4'-aminodiphenylamine-6-sulfonic acid, Na salt

A mixture of 10 g 2-chloro-3,5-dinitrobenzene sulfonic acid, Na salt (0.034 mol), 3.7 g p-phenylenediamine (0.034 mol) and 2.4 g potassium carbonate (0.017 mol) in 75 ml water was refluxed for 2 hours. After cooling, the deposit was filtered off. Red-brown crystals.

Melting point above 305° C.

19.
2,4-dinitro-2'-chloro-4'-aminodiphenylamine-6-sulfonic acid, Na salt Preparation was carried out in the same way as in Example 18, except that 4.1 g 2-chloro-p-phenylenediamine (0.017 mol) was used instead of p-phenylenediamine. Brown crystals.

Melting point above 305° C.

20. 2,4-dinitro-4'-hydroxydiphenylamine-6-sulfonic acid, Na salt

Preparation was carried out in the same way as in Example 18, except that 1.86 g p-aminophenol (0.017 mol) was used instead of p-phenylenediamine. Brown crystals.

Melting point above 305° C.

21.
2,4-dinitro-4'-N-ethyl-N-β-hydroxyethylaminodiphenylamine-6-sulfonic acid, Na salt Preparation was carried out in the same way as in Example 18 except that 4.7 g N-ethyl-N-β-hydroxyethyl-p-phenylenediamine (0.017 mol) was used instead of p-phenylenediamine. Black crystals.

Melting point above 160° C. (with decomposition).

22.
2,4-dinitro-2'-methyl-4'-aminodiphenylamine-6-sulfonic acid, Na salt Preparation was carried out in the same way as in Example 18, except that 3.75 g p-tolylenediamine sulfate (0.017 mol) was used instead of p-phenylenediamine. Red-brown crystals.

Melting point above 305° C.

23.
2,4-dinitro-4'-N,N-bis-(β-hydroxyethyl)-aminodiphenylamine-6-sulfonic acid, Na salt Preparation was carried out in the same way as in Example 18 except that 4.6 g N,N-bis-(β-hydroxyethyl)-p-phenylenediamine (0.017 mol) was used instead of p-phenylenediamine. Black crystals.

Melting point 174° C.

The following compounds known from the literature were additionally included in the hair-dyeing tests:

24. 2,4-dinitrodiphenylamine-6-sulfonic acid, Na salt (Ann. 366, 83 (1909))

25. 2,6-dinitrodiphenylamine-4-carboxylic acid (Am. Chem. J. 19, 18 (1897))

26. 2,6-dinitrodiphenylamine-4-sulfonic acid (Ann. 366, 106 (1909))

Hair-dyeing tests

Hair dye creams were prepared from the following constituents:

| | |
|---|---|
| $C_{12-18}$ fatty alcohol | 10 g |
| $C_{12-14}$ fatty alcohol + 2 E.O. sulfate, Na salt (28%) | 25 g |
| Water | 60 g |
| Substantive dye (Nos. 1-26, above) | 1 g |
| Ammonium sulfate | 1 g |
| Concentrated ammonium solution | to pH = 9.5 |
| Water q.s. ad | 100 g |

The constitutents were mixed together in the above order. After addition of the substantive dyes, the pH-value of the emulsion was first adjusted to 9.5 with concentrated ammonia solution, after which the emulsion was made up with water to 100 g.

The dye cream was applied to about 5 cm long strands of standardized, 90% gray, but not specially pretreated human hair and left thereon for 30 minutes at 27° C. After dyeing, the hair was rinsed, washed with a standard shampoo and then dried.

The compounds of Examples 1 to 26 were used as substantive dyes.

The results of the dyeing tests are shown in Table I below.

TABLE I

| Substantive dye of Example No. | Color of the dyed hair |
|---|---|
| 1 | brown |
| 2 | orange-brown |
| 3 | brown |
| 4 | orange-brown |
| 5 | brown |
| 6 | orange-brown |
| 7 | orange-brown |
| 8 | chestnut brown |
| 9 | light brown |
| 10 | orange yellow |
| 11 | brown |

TABLE I-continued

| Substantive dye of Example No. | Color of the dyed hair |
| --- | --- |
| 12 | hair brown |
| 13 | yellow |
| 14 | brown |
| 15 | brown |
| 16 | brown |
| 17 | yellow |
| 18 | topaz yellow |
| 19 | apricot yellow |
| 20 | gold yellow |
| 21 | light brown |
| 22 | copper |
| 23 | cognac brown |
| 24 | olive yellow |
| 25 | deep yellow |
| 26 | yellow |

We claim:

1. A hair dyeing preparation comprising a cosmetic carrier, an anionic, nonionic or ampholytic surfactant present in an effective amount as a wetting agent and emulsifier, oxidation hair dye precursors present in a total quantity of 0 to 5% by weight, a first substantive hair dye present in a quantity of about 0.01–5.0% by weight, and a second substantive hair dye other than according to formula I present in 0 to 5% by weight, all percentages based upon the total weight of the preparation, said first substantive hair dye consisting essentially of at least one nitrodiphenylamine compound of the formula:

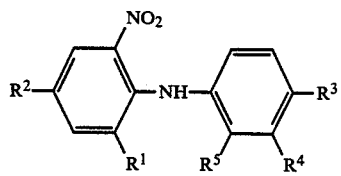

wherein:
(A) one of $R^1$ or $R^2$ is nitro and the other is —$SO_3H$ or —COOH; and
(B)
(1) $R^3$, $R^4$, and $R^5$ are, independently of one another, hydrogen or a $C_{1-4}$ alkyl; or
(2) two of $R^3$, $R^4$, and $R^5$ are, independently of one another, hydrogen or a $C_{1-4}$ alkyl, and the remaining is hydroxyl or —$NR^6R^7$ were $R^6$ and $R^7$ are, independently of one another, hydrogen, a $C_{1-4}$ alkyl, or a $C_{2-4}$ hydroxyalkyl; or
(3) one of $R^3$, $R^4$, or $R^5$ is hydrogen or a $C_{1-4}$ alkyl, another is hydroxyl or $NR^6R^7$ where $R^6$ and $R^7$ are, independently of one another, hydrogen a $C_{1-4}$ alkyl, or a $C_{2-4}$ hydroxyalkyl, and the remaining is hydroxymethyl, a $C_{1-4}$ alkoxy, or chlorine;
or their water-soluble salts.

2. A hair dyeing preparation comprising a cosmetic carrier, oxidation hair dye precursors present in a total quantity of 0 to 5% by weight, a first substantive hair dye present in a quantity of about 0.01–5.0% by weight, and a second substantive hair dye other than according to formula I present in 0 to 5% by weight, all percentages based upon the total weight of the preparation, said first substantive hair dye consisting essentially of at least one nitrodiphenylamine compound of the formula:

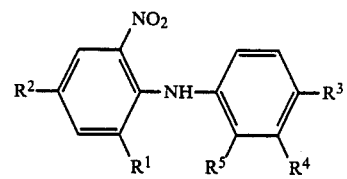

wherein:
(A) one of $R^1$ or $R^2$ is nitro and the other is 13 $SO_3H$ or —COOH; and
(B) one of $R^3$, $R^4$, or $R^5$ is hydrogen or a $C_{1-4}$ alkyl, another is hydroxyl or $NR^6R^7$ were $R^6$ and $R^7$ are, independently of one another, hydrogen, a $C_{1-4}$ alkyl, or a $C_{2-4}$ hydroxyalkyl, and the remaining is hydroxymethyl, a $C_{1-4}$ alkoxy, or chlorine;
or their water-soluble salts.

3. The preparation of claim 1 wherein substituents $R^3$, $R^4$ and $R^5$ are according to (B)(1).

4. The preparation of claim 1 wherein substituents $R^3$, $R^4$ and $R^5$ are according to (B)(2).

5. The preparation of claim 1 wherein substituents $R^3$, $R^4$ and $R^5$ are according to (B)(3).

6. The preparation of claim 1 wherein said nitrodiphenylamine compound is in the form of a water soluble salt of sodium, potassium, ammonium, or a $C_{2-4}$-alkanolammonium.

7. The preparation of claim 1 wherein
$R^3$ is: hydroxy, amino, methylamino, dimethylamino, diethylamino, N-ethyl-N-$\beta$-hydroxy ethylamino, or N,N-bis-($\beta$-hydroxyethyl)amino;
$R^4$ is: hydrogen, methyl, dimethyl, or hydroxymethyl; and
$R^5$ is: hydrogen, methyl, methoxy, or chlorine.

8. The preparation of claim 1 wherein said nitrodiphenylamine compound is:
2,6-dinitro-4'-dimethylaminodiphenylamine-4-sulfonic acid, K-salt.

9. The preparation of claim 1 wherein said nitrodiphenylamine compound is:
2,6-dinitro-4'-aminodiphenylamine-4-sulfonic acid, K-salt.

10. The preparation of claim 1 wherein said nitrodiphenylamine compound is:
2,6-dinitro-4'-methylamino diphenylamine-4-sulfonic acid, K-salt.

11. The preparation of claim 2 wherein said nitrodiphenylamine compound is:
2,6-dinitro-2'-methyl-4'-aminodiphenylamine-4-sulfonic acid, K-salt.

12. The preparation of claim 2 wherein said nitrodiphenylamine compound is:
2,6-dinitro-4'-N,N-bis-($\beta$-hydroxyethyl)-aminodiphenyl-amine-4-sulfonic acid, K-salt.

13. The preparation of claim 2 wherein said nitrodiphenylamine compound is:
2,6-dinitro-2'-chloro-4'-aminodiphenylamine-4-sulfonic acid, K-salt.

14. The preparation of claim 2 wherein said nitrodiphenylamine compound is:
2,6-dinitro-2',3'-dimethyl-4'-aminodiphenylamine-4-sulfonic acid, K-salt.

15. The preparation of claim 2 wherein said nitrodiphenylamine compound is:
2,6-dinitro-3'-hydroxymethyl-4'-aminodiphenylamine-4-sulfonic acid, K-salt.

16. The preparation of claim 2 wherein said nitrodiphenylamine compound is:
2,6-dinitro-2'-methoxy-4'-aminodiphenylamine-4-sulfonic acid, K-salt.

17. The preparation of claim 1 wherein said nitrodiphenylamine compound is:
2,6-dinitro-4'-hydroxydiphenylamine-4-sulfonic acid, K-salt.

18. The preparation of claim 2 wherein said nitrodiphenylamine compound is:
2,6-dinitro-4'-N-ethyl-N-β-hydroxethylaminodiphenylamine-4-sulfonic acid, K-salt.

19. The preparation of claim 2 wherein said nitrodiphenylamine compound is:
2,6-dinitro-2'-methyl-4'-N,N-diethylaminodiphenylamine-4-sulfonic acid, K-salt.

20. The preparation of claim 1 wherein said nitrodiphenylamine compound is:
2,4-dinitro-4'-dimethylaminodiphenylamine-4-carboxylic acid.

21. The preparation of claim 1 wherein said nitrodiphenylamine compound is:
2,6-4'-aminodiphenylamine-4-carboxylic acid.

22. The preparation of claim 2 wherein said nitrodiphenylamine compound is:
2,6-dinitro-4'-amino-3'-methyldiphenylamine-4-carboxylic acid.

23. The preparation of claim 1 wherein said nitrodiphenylamine compound is:
2,6-dinitro-4'-N,N-dimethylaminodiphenylamine-4-carboxylic acid.

24. The preparation of claim 1 wherein said nitrodiphenylamine compound is:
2,6-dinitro-4'-hydroxydiphenylamine-4-carboxylic acid.

25. The preparation of claim 1 wherein said nitrodiphenylamine compound is:
2,4-dinitro-4'-aminodiphenylamine-6-sulfonic acid, Na salt.

26. The preparation of claim 2 wherein said nitrodiphenylamine compound is:
2,4-dinitro-2'-chloro-4'-aminodiphenylamine-6-sulfonic acid, Na salt.

27. The preparation of claim 1 wherein said nitrodiphenylamine compound is:
2,4-dinitro-4'-hydroxydiphenylamine-6-sulfonic acid, Na salt.

28. The preparation of claim 2 wherein said nitrodiphenylamine compound is:
2,4-dinitro-4'-N-ethyl-N-β-hydroxyethylaminodiphenyl-amine-6-sulfonic acid, Na salt.

29. The preparation of claim 2 wherein said nitrodiphenylamine compound is:
2,4-dinitro-2'-methyl-4'-aminodiphenylamine-6-sulfonic acid, Na salt.

30. The preparation of claim 2 wherein said nitrodiphenylamine compound is:
2,4-dinitro-4'-N,N-bis-(β-hydroxyethyl)-aminodiphenylamine-6-sulfonic acid, Na salt.

31. The preparation of claim 1 wherein said nitrodiphenylamine compound is:
2,4-dinitrodiphenylamine-6-sulfonic acid, Na salt.

32. The preparation of claim 1 wherein said nitrodiphenylamine compound is:
2,6-dinitrodiphenylamine-4-carboxylic acid.

33. The preparation of claim 1 wherein said nitrodiphenylamine compound is:
2,6-dinitrodiphenylamine-4-sulfonic acid.

34. A method for using the preparation of claim 1 comprising applying it to hair, leaving it thereon until color is imparted, and then rinsing the hair with water.

35. A nitrodiphenylamine compound of the formula:

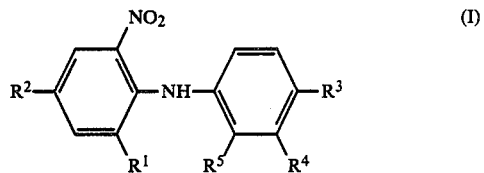

wherein:
(A) one of $R^1$ or $R^2$ is nitro and the other is —$SO_3H$ or —COOH; and
(B) $R^3$ is hydroxyl or $NR^6R^7$ where $R^6$ and $R^7$ are, independently of one another, hydrogen, a $C_{1-4}$ alkyl, or a $C_{2-4}$ hydroxyalkyl; and
(C) one of $R^4$ or $R^5$ is hydrogen or a $C_{1-4}$ alkyl, and the other is hydroxymethyl, a $C_{1-4}$ alkoxy, or chlorine;
or a water-soluble salt thereof.

36. A hair dyeing preparation comprising a cosmetic carrier, oxidation hair dye precursors present in a total quantity of 0 to 5% by weight, a first substantive hair dye present in a quantity of about 0.01–5.0% by weight, and a second substantive hair dye other than according to formula I present in 0.01 to 5% by weight, all percentages based upon the total weight of the preparation, said first substantive hair dye consisting essentially of at least one nitrodiphenylamine compound of the formula:

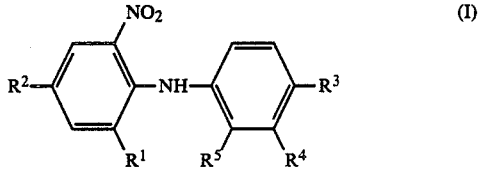

wherein:
(A) one of $R^1$ or $R^2$ is nitro and the other is —$SO_3H$ or —COOH; and
(B)
(1) $R^3$, $R^4$, are, independently of one another, hydrogen or a $C_{1-4}$ alkyl; or
(2) two of $R^3$, $R^4$, and $R^5$ are, independently of one another, hydrogen or a $C_{1-4}$ alkyl, and the remaining is hydroxyl or —$NR^6R^7$ where $R^6$ and $R^7$ are, independently of one another, hydrogen, a $C_{1-4}$ alkyl, or a $C_{2-4}$ hydroxyalkyl; or
(3) one of $R^3$, $R^4$, or $R^5$ is hydrogen or a $C_{1-4}$ alkyl, another is hydroxyl or $NR^6R^7$ where $R^6$ and $R^7$ are, independently of one another, hydrogen, a $C_{1-4}$ alkyl, or a $C_{2-4}$ hydroxyalkyl, and the remaining is hydroxymethyl, a $C_{1-4}$ alkoxy, or chlorine;
or their water-soluble salts.

* * * * *